(12) United States Patent
Hayman (10) Patent No.: US 10,893,880 B1
(45) Date of Patent: Jan. 19, 2021

(54) BODY-SPECIFIC DERMA ROLLER

(71) Applicant: Hillary Hayman, Los Angeles, CA (US)

(72) Inventor: Hillary Hayman, Los Angeles, CA (US)

(73) Assignee: Elyse Enterprises LLC, Los Angeles, CA (US)

( * ) Notice: Subject to any disclaimer, the term of this patent is extended or adjusted under 35 U.S.C. 154(b) by 0 days.

(21) Appl. No.: 17/012,876

(22) Filed: Sep. 4, 2020

(51) Int. Cl.
| | |
|---|---|
| *A61B 17/06* | (2006.01) |
| *A61B 17/20* | (2006.01) |
| *A61B 17/062* | (2006.01) |
| *A61H 15/00* | (2006.01) |
| *A61M 37/00* | (2006.01) |
| *A61B 17/00* | (2006.01) |

(52) U.S. Cl.
CPC .......... *A61B 17/205* (2013.01); *A61B 17/062* (2013.01); *A61H 15/0092* (2013.01); *A61M 37/0015* (2013.01); *A61B 2017/00747* (2013.01); *A61B 2017/00761* (2013.01); *A61H 2015/0007* (2013.01); *A61H 2015/0014* (2013.01); *A61M 2037/003* (2013.01); *A61M 2037/0023* (2013.01); *A61M 2037/0038* (2013.01)

(58) Field of Classification Search
CPC ...... A61M 37/0015; A61M 2037/0023; A61M 2037/003; A61M 2037/0038; A61H 15/00; A61H 15/0092; A61H 2015/0007; A61H 2015/0014; A61B 2017/00747; A61B 2017/00761

See application file for complete search history.

(56) References Cited

U.S. PATENT DOCUMENTS

| | | | | |
|---|---|---|---|---|
| 1,630,149 | A | * | 5/1927 | Wahrt ...................... D21C 3/26 601/119 |
| 6,994,680 | B1 | * | 2/2006 | Aponte ................... A61H 7/005 601/136 |
| 8,376,984 | B2 | | 2/2013 | James |
| D766,454 | S | * | 9/2016 | Higgins ....................... D24/214 |
| 2006/0276732 | A1 | * | 12/2006 | Chen .................. A61H 15/0092 601/113 |
| 2018/0161234 | A1 | * | 6/2018 | Dominee ........... A61H 15/0092 |

* cited by examiner

*Primary Examiner* — Todd J Scherbel
(74) *Attorney, Agent, or Firm* — Patent Ingenuity, P.C.; Samuel K. Simpson (57) ABSTRACT

A derma roller apparatus has a head, which has a cylindrical member and a plurality of needles situated around the cylindrical member. The width of the cylindrical member may be in a range of four to twelve inches. Furthermore, each of the plurality of needles may have a length of at least five tenths millimeters. In addition, the derma roller apparatus has a swivel, a connector, and a handle. The connector connects to a first endpoint of the head and a second endpoint of the head. Furthermore, the handle is operably attached to the connector via the swivel. The handle is configured to move along a yaw axis with respect to a collinear plane that is collinear with the head and the handle. Finally, the first endpoint and the second endpoint of the head are transverse to the collinear plane. As an alternative, the handle may be telescopic.

17 Claims, 11 Drawing Sheets

FIG. 8

BODY-SPECIFIC DERMA ROLLER

BACKGROUND

1. Field

This disclosure generally relates to skincare apparatuses. More particularly, the disclosure relates to a derma roller.

2. General Background

Many people seek to improve the appearance of their skin for a variety of reasons. For some, it is a matter of aesthetics, while for others, it is a matter of necessity. For instance, some people may want to improve the appearance of their skin via various plastic surgery or dermatology procedures (e.g., facelift, jaw lift, eye wrinkle reduction, etc.) to rejuvenate the appearance of their skin. And others may require these procedures to diminish or eliminate the effects (e.g., scar tissue, burns, etc.) from injuries.

Irrespective of the particular motivation for undergoing plastic surgery or dermatology procedures, patients often face a number of risks. In some instances, those undergoing plastic surgery procedures may end up with significant disfiguration. Although the skill and experience of the plastic surgeon may play a part, other factors, such as the way the skin heals for different people, may also lead to potential disfiguration. Ultimately, plastic surgery procedures often involve significant levels of invasiveness that may injure the skin of the user.

With respect to rejuvenating portions of the body, many users are willing to accept the foregoing risks. In particular, many users do not have the manual dexterity to utilize various skincare devices on their own for application to hard-to-reach areas, such as the back. As a result, many users subject themselves to costly and risky skincare procedures.

SUMMARY

In one embodiment, a derma roller apparatus is provided. The derma roller apparatus has a head, which has a cylindrical member and a plurality of needles situated around the cylindrical member. The width of the cylindrical member may be in a range of four to twelve inches. Furthermore, each of the plurality of needles may have a length of at least five tenths millimeters.

In addition, the derma roller apparatus has a swivel, a connector, and a handle. The connector connects to a first endpoint of the head and a second endpoint of the head. Furthermore, the handle is operably attached to the connector via the swivel. The handle is configured to move along a yaw axis with respect to a collinear plane that is collinear with the head and the handle. Finally, the first endpoint and the second endpoint of the head are transverse to the collinear plane.

As an alternative, the handle may be telescopic. One or more actuators may activate extension and retraction of the handle. For example, a first actuator may activate extension of the handle; whereas, a second actuator may activate retraction of the handle. The one or more actuators may be positioned on the handle, or some other portion of the derma roller apparatus, such as the connector.

Finally, the derma roller apparatus may also have one or more stoppers that restrict movement of the handle within a predetermined angular range along the yaw axis.

BRIEF DESCRIPTION OF THE DRAWINGS

The above-mentioned features of the present disclosure will become more apparent with reference to the following description taken in conjunction with the accompanying drawings wherein like reference numerals denote like elements and in which.

DETAILED DESCRIPTION

A body-specific derma roller is provided to allow users to perform skincare rejuvenation on body parts other than the face, without having to visit a dermatologist's or plastic surgeon's office. The body-specific derma roller allows a user, who may not have the manual dexterity to position a derma roller in hard-to-reach areas of the body (e.g., the back) to perform skincare rejuvenation. In particular, the body-specific derma roller has a swivel that allows the user to change the angular displacement along one axis, while at the same time moving the head of the derma roller along a linear path on another axis. For example, a user may not have the manual dexterity to reach his or her back with a conventional derma roller. By way of contrast, the body-specific derma roller allows the user to vertically move the derma roller up and down the back area, while also allowing the user to change the angle of the handle in a horizontal plane during that vertical motion. In essence, the user is able to hold the handle outside of the trunk area, and maneuver the head of the body-specific derma roller for application to the trunk area. During motion along the linear path of the head of the body-specific derma roller, the user may adjust the horizontal angular displacement of the handle to provide optimal comfort to the user.

Accordingly, the angular displacement along one axis in conjunction with the linear motion along another axis provide for flexibility and stability during user application. The linear motion of the head of the derma roller allows for optimal skincare rejuvenation by minimizing patches of skin not being punctured via the needles adhered to the head of the body-specific derma roller.

In addition, in contrast with conventional derma roller head configurations, which are typically two inches in width, the body-specific derma roller has a head that is in the range of four to twelve inches. (Although the range of four to twelve inches is provided, a greater width (e.g., fifty inches) may be utilized to cover more space, such as for a non-human.) By having a wider derma roller head, the body-specific derma roller allows for optimal coverage of portions of the body, which typically encompass a larger area than the face. Furthermore, the wider derma roller head allows for faster application, since fewer derma roller head movements are necessary. For example, in contrast with a conventional two-inch derma roller head, the twelve-inch body-specific derma roller may cover the same area with one sixth, or less, of the total movements performed with a conventional derma roller. The reason that the body-specific derma roller may accomplish the same coverage with even less strokes than one-sixth of the movements is that the conventional derma roller may necessitate overlapping movements to ensure that the entire area (e.g., the back) has been derma rolled.

In essence, the body-specific derma roller tightens, tones, and lifts the skin of various portions of the body, including areas that are typically hard to reach, while concurrently allowing for flexible, yet firm control by the user.

Figure 1:
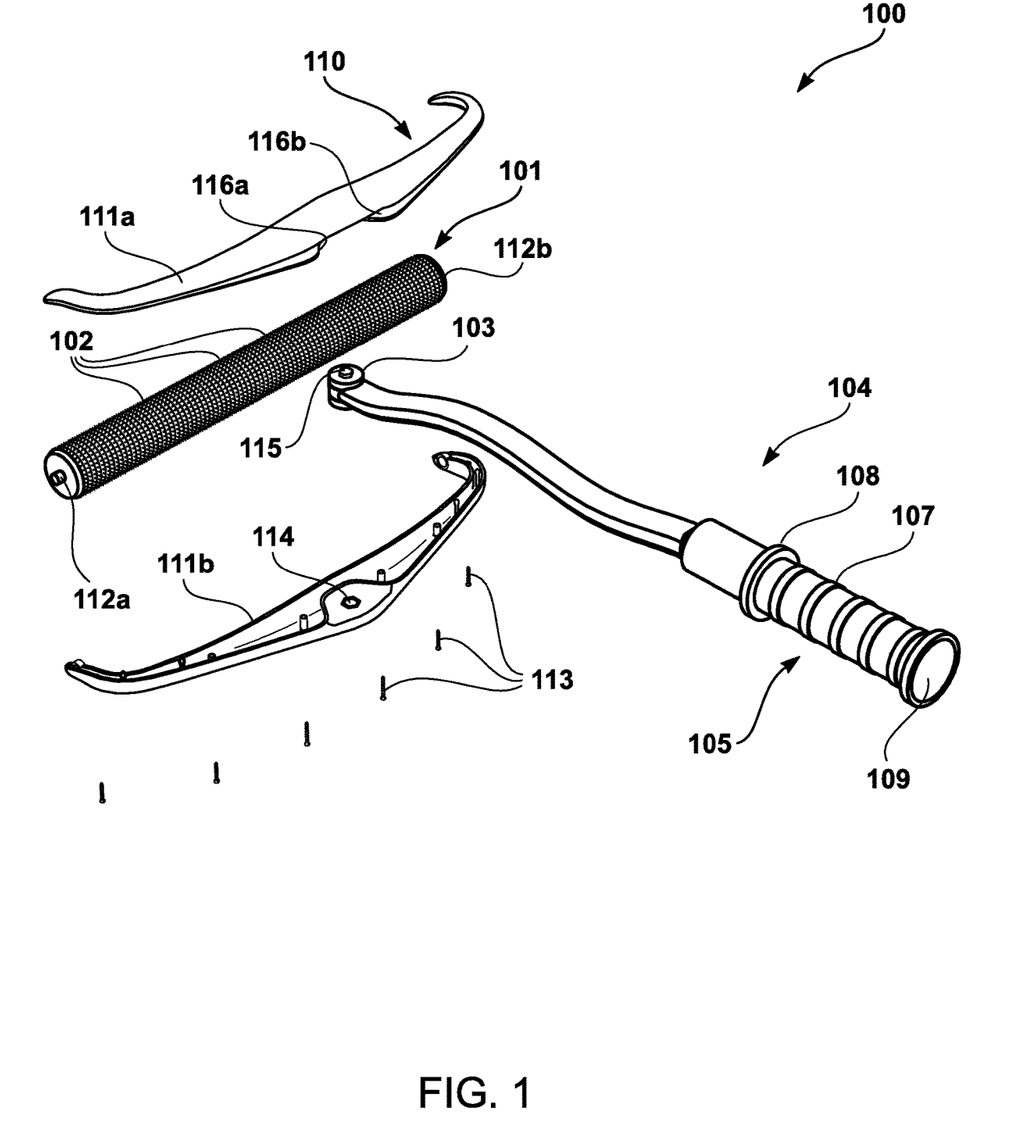
FIG. 1 illustrates a disassembly view of a body-specific derma roller apparatus.

FIG. 1 illustrates a disassembly view of a body-specific derma roller apparatus 100. In particular, the body-specific derma roller apparatus 100 may have a head 101 on which a plurality of needles 102 are situated. In one embodiment, the head 101 is a cylindrical member that rotates as a user moves the body-specific derma roller apparatus 100 along a skin surface. Accordingly, the plurality of needles 102 may be positioned around the head 101 to allow for rotational movement of the plurality of needles 102 along the skin surface, thereby creating a plurality of skin punctures to promote skincare rejuvenation (e.g., through collagen production). Given that the body-specific derma roller apparatus 100 is applied to the body rather than the face, which is typically more sensitive given thinner layers of skin in that area, the body-specific derma roller apparatus 100 may have a plurality needles that are longer than those conventionally utilized for the face. For example, whereas a minimum needle length for the face is typically one quarter of a millimeter, a minimum needle length for the body may have a minimum length of five tenths millimeters. Since the skin on the body tends to be thicker and more durable than the face, the maximum needle length may be as much as two millimeters.

Additionally, the body-specific derma roller apparatus 100 may have a handle 104 that a user may utilize to perform movements of the body-specific derma roller apparatus 100. Specifically, the body-specific derma roller apparatus 100 may have a gripping portion 105 that allows for easy gripping of the handle 104. To avoid a hand of the user from slipping during operation of the body-specific derma roller apparatus 100, one or portions, or the entirety of, the gripping portion 105 may have one or more ribbed, or elevated, surfaces 107 to allow for better gripping of the handle 104 than a smooth surface. As yet another addition, or alternative, the handle 104 may have a grip guard 108 and/or a pommel 109. Accordingly, even if the hand of the user was to slip on the gripping portion 105, the grip guard 108 prevents the hand from upward movement toward the plurality of needles 102; conversely, the pommel 109 prevents the hand from downward movement off of the gripping portion 105. Given the large quantity of needles potentially positioned around the head 101 that may be four to twelve inches in width, and the user possibly not fully seeing where the body-specific derma roller apparatus 100 is at all times (e.g., application of the body-specific derma roller apparatus 100 to the back), the foregoing features provide an added level of safety during body derma rolling.

Additionally, the body-specific derma roller apparatus 100 has a connector 110 that connects to a first endpoint 112a (e.g., left endpoint) of the head 101 and a second endpoint 112b (e.g., right endpoint) of the head 101. Although the connector 110 connects to each endpoint 112a and 112b, the head 101 may still freely move about its rotational axis; in other words, the connector 110 does not impede rotational movement of the head 101. Furthermore, in one embodiment, the connector 110 may have a top portion 111a and a bottom portion 111b that may be adhered to one another. For example, one or more screws 113 may be utilized to adhere the top portion 111a and the bottom portion 111b together. (Other types of adherent mechanisms (e.g., pins, bolts, clips, magnets, etc.) or adherents (e.g., glue) may be utilized instead of screws.)

In one embodiment, the connector 110 may have one or more swivel cavities 114 that interface with one or more swivel protrusions 115 to connect a swivel 103 to the connector 110. The swivel 103 is also connected, or integrated within, the handle 104 to allow for movement of the handle 104 with respect to the to the derma roller head 101. In essence, the swivel 103 allows a user to comfortably adjust the handle 104 without moving the head 101 off of a linear path during derma rolling. Given that many users will not have the manual dexterity to hold the handle 104 in a position that is perpendicular to the head 101 during derma rolling of certain body areas (e.g., back), the swivel 103 allows those users to move the handle 104 to effectively enhance the manual dexterity of the user during body derma rolling.

In one embodiment, a left wall 116a of the connector 110 and a right wall 116b of the connector 110 act as stoppers to restrict movement of the handle 104 to that of a predetermined angular displacement (e.g., forty-five degrees). (Other angular displacements may be utilized instead of forty-five degrees.) For instance, the angulation of the walls 116a and 116b may correspond to the predetermined angular displacement (e.g., approximately forty-five degree angulation of the walls 116a and 116b to match a predetermined angular displacement of forty-five degrees.). By restricting the angulation of the handle 104, the user is able to move the handle 104 in a stable manner without too much movement (i.e., close to parallel with the head 101), which could otherwise compromise the operability of the body-specific derma roller apparatus 100. In essence, the connector 110 acts as a housing for the swivel 103, which is connected to the handle 104 through an opening of the connector 110. In an alternative embodiment, different stoppers may be utilized to restrict the angulation. For example, instead of the walls 116a and 116b acting as stoppers, one or more adjustable prongs may be positioned to the side of the swivel 103. The user may then activate one or more actuators that adjust the positioning of the prongs to different locations within the connector 110, thereby adjusting the possible angulation of the handle 104.

Figure 2:
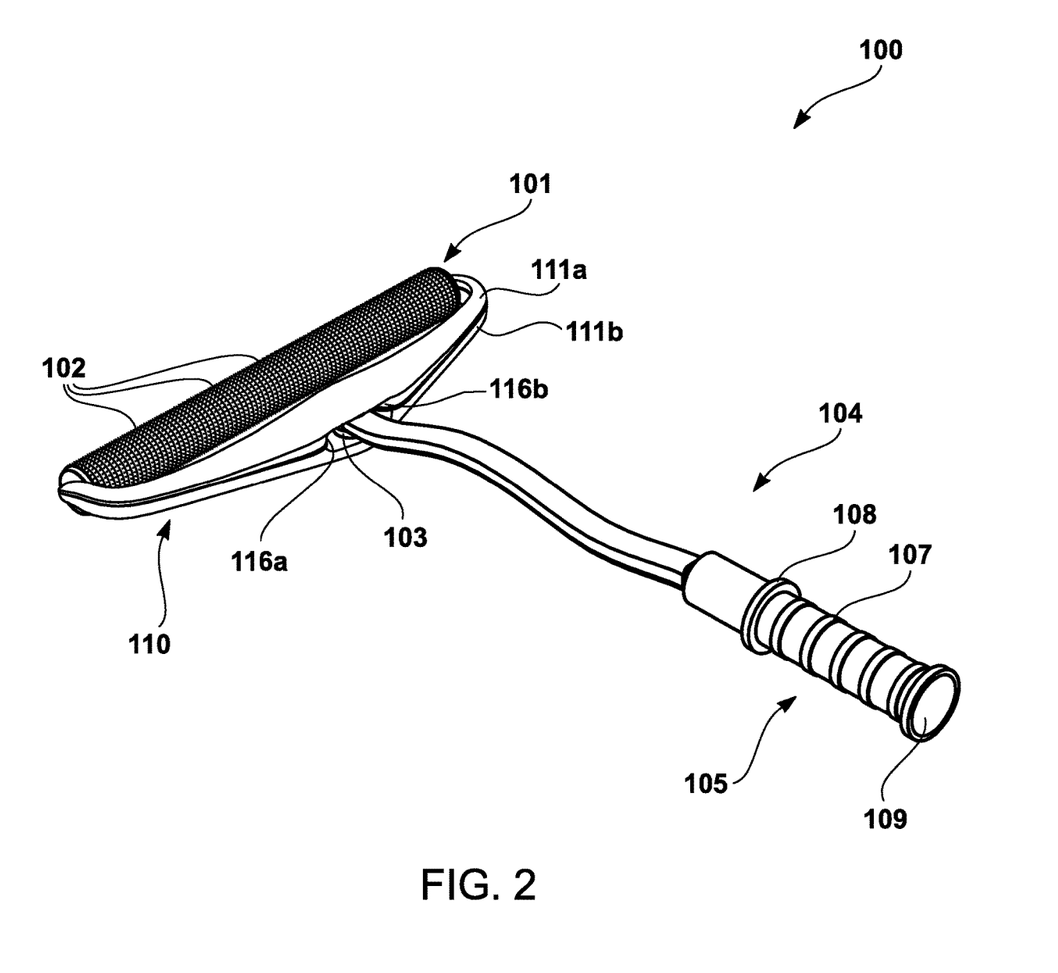
FIG. 2 illustrates an assembly view of the body-specific derma roller apparatus illustrated in FIG. 1.
Figure 3A:
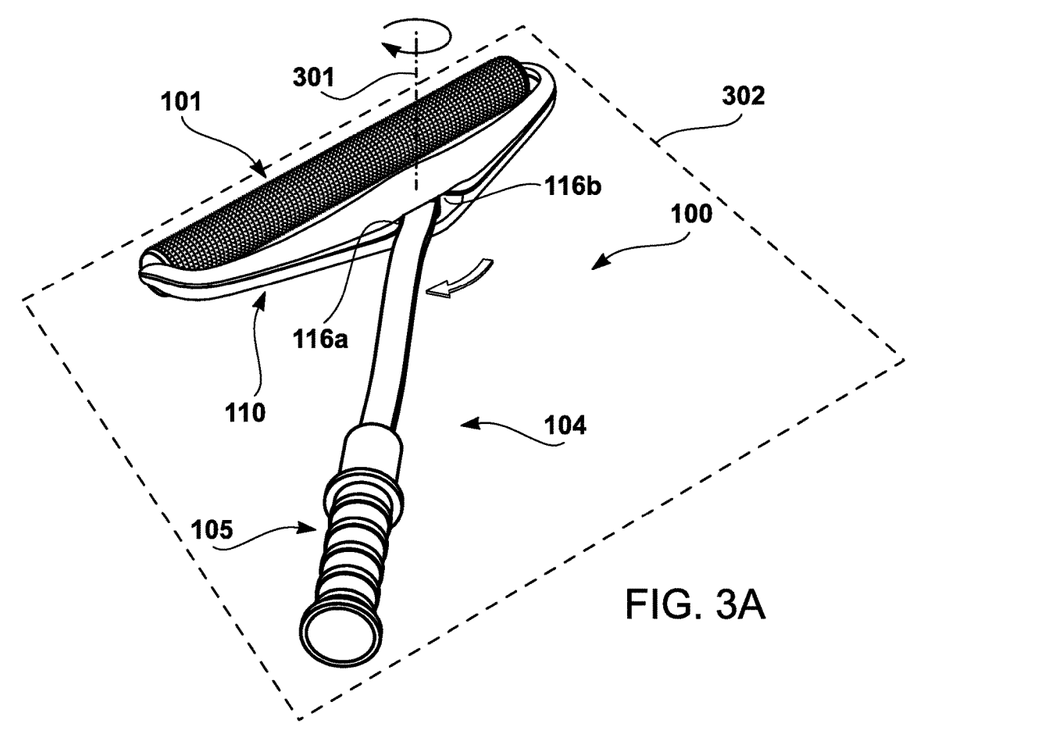
FIG. 3A illustrates an approximate forty-five degree rotation to the left about a yaw axis.
Figure 3B:
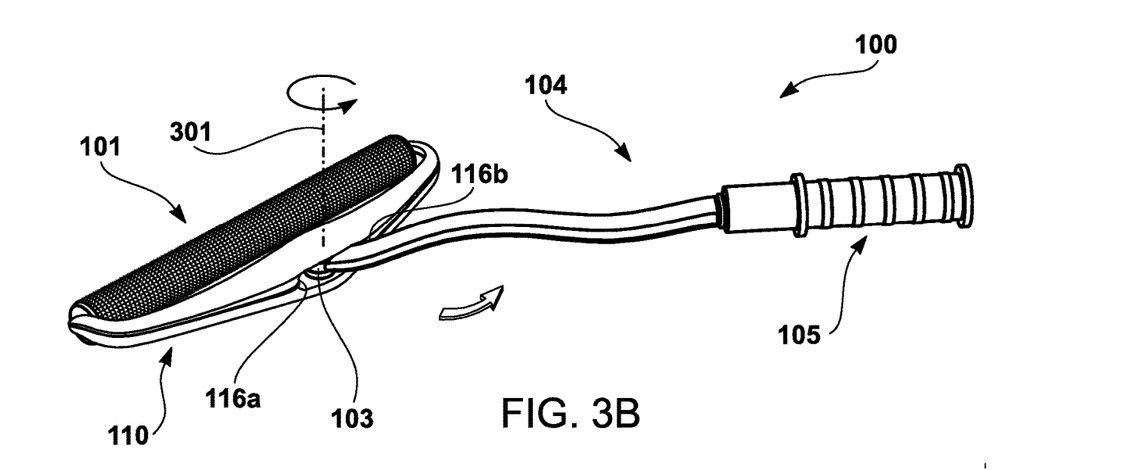
FIG. 3B illustrates an approximate forty-five degree rotation to the right about the yaw axis.

FIG. 2 illustrates an assembly view of the body-specific derma roller apparatus 100 illustrated in FIG. 1. Furthermore, FIGS. 3A and 3B illustrate rotation of the handle 104 with respect to the head 101. For example, FIG. 3A illustrates an approximate forty-five degree rotation to the left about a yaw axis 301. (The angle of forty-five degrees is illustrated only as an example—other angles may be utilized.) Furthermore, the yaw axis 301 is perpendicular, or approximately perpendicular, to a collinear plane 302 that is collinear with the head 101 and the handle 104. Furthermore, the first endpoint 112a and the second endpoint 112b of the head are transverse to the collinear plane 302. Accordingly, even as the head 101 moves along a linear path (e.g., up and down a patch of skin), the rotation of the handle 104 about the yaw axis 301 does not impede the linear movement of the head 101 over the skin of the user; rather, it allows the user to adjust his or her hand during the linear movement of the head 101 to provide more comfort to the user. Through the linear movement of the head 101, the user may even adjust the angulation of the handle 104 multiple times to different angles about the yaw axis 301. Conversely, FIG. 3B illustrates an approximate forty-five degree rotation to the right about the yaw axis 301.

In one embodiment, the swivel 103 is configured to rotate only about the yaw axis 301 without rotation about a pitch axis and a roll axis during movement of the body-specific derma roller apparatus 100 along the skin of a user. By restricting the angulation to rotation about one axis, the body-specific derma roller apparatus 100 provides stability with respect the linear movement of the head 101, while also allowing for the handle 104 to provide enhanced dexterity to the user.

Figure 4A:
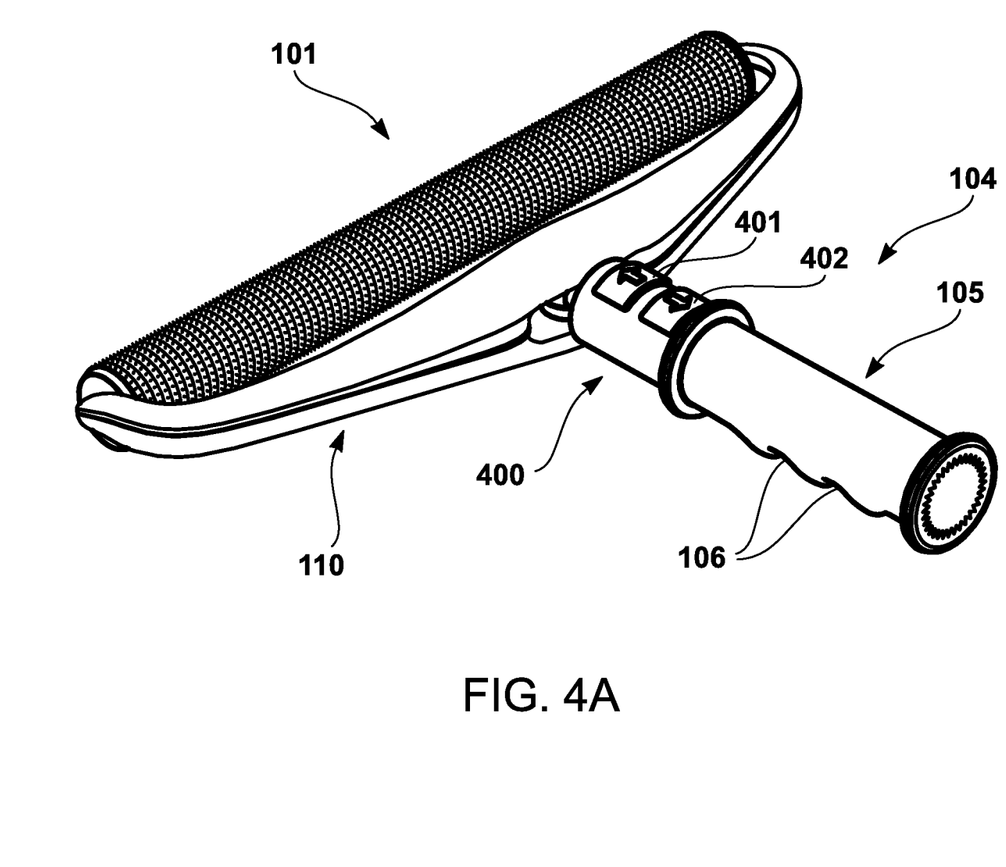
FIG. 4A illustrates the telescopic body-specific derma roller apparatus in a retracted state.
Figure 4B:
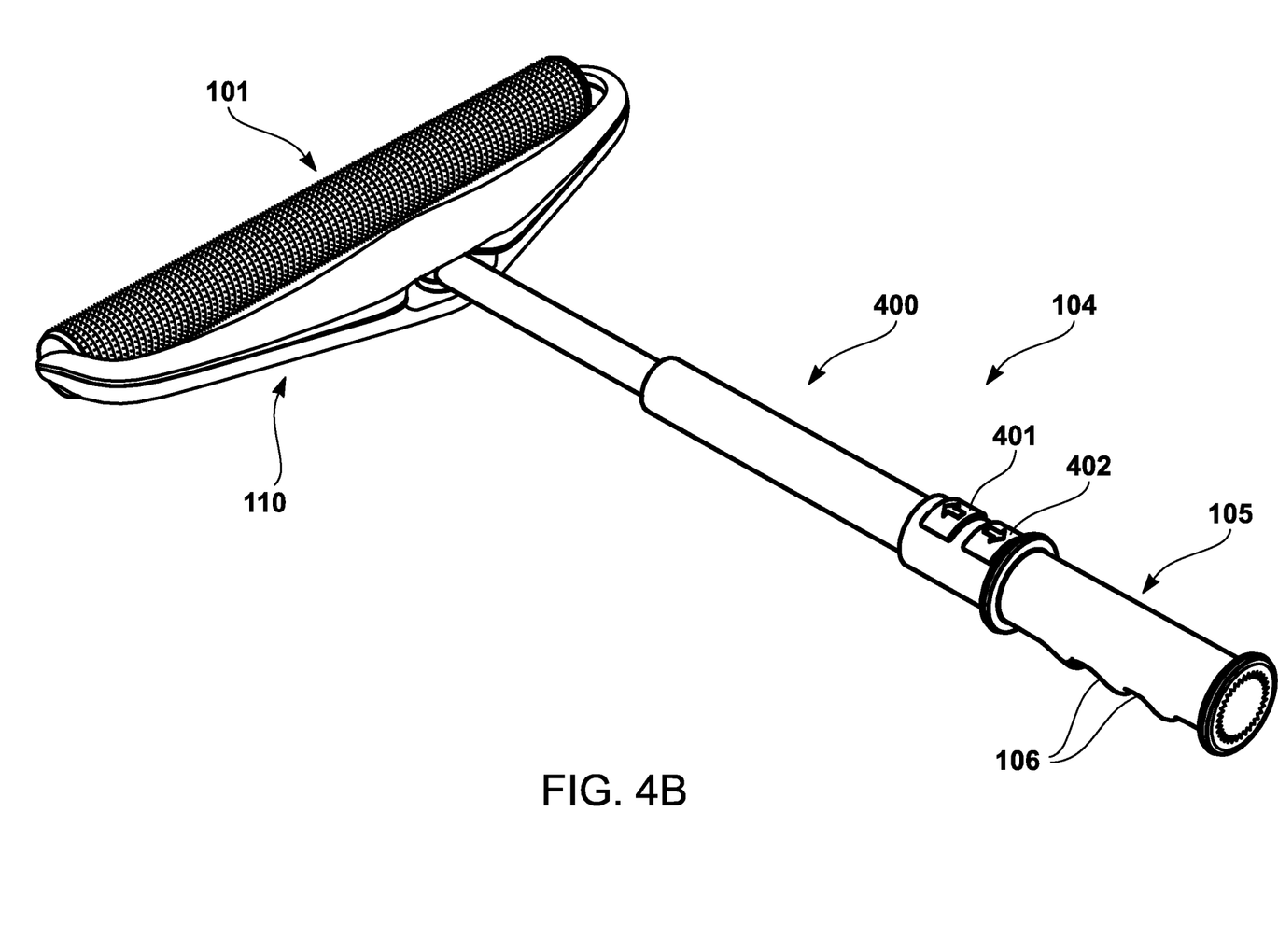
FIG. 4B illustrates the telescopic body-specific derma roller apparatus in an extended state.

FIGS. 4A and 4B illustrate a telescopic body-specific derma roller apparatus 400. In particular, FIG. 4A illustrates the telescopic body-specific derma roller apparatus 400 in a retracted state. The handle 104 may have one or more actuators to retract and extend the telescopic body-specific derma roller apparatus 400. For example, a retraction actuator 401 (e.g., button, dial, etc.) may be activated to retract a significant portion of the handle 104 into the gripping portion 105. In one embodiment, the retraction actuator 401 may be a mechanical device that, when activated, allows the user to manually retract the handle 104. In another embodiment, the retraction actuator 401 is an electromechanical device that, when activated, sends an electrical signal to automatically perform the retraction for the user. Conversely, an extension actuator 402 may be activated to perform an extension. For example, the extension actuator 402 may be a spring-loaded device that, when activated, promulgates the handle 104 forward into full extension. Alternatively, the extension actuator 402 may be an electromechanical device that, when activated, sends an electrical signal to automatically perform the extension for the user. FIG. 4B illustrates the telescopic body-specific derma roller apparatus 400 in an extended state. Although two different actuators are illustrated in FIGS. 4A and 4B, a single actuator may be utilized instead to perform both retraction and extension (i.e., extension and retraction alternate with each activation).

The gripping portion 105 may have one or more finger grooves 106. The ribbed surfaces 107, illustrated in FIG. 1, or the finger grooves 106 may be utilized separately or together with any of the configurations provided for herein.

Figure 5A:
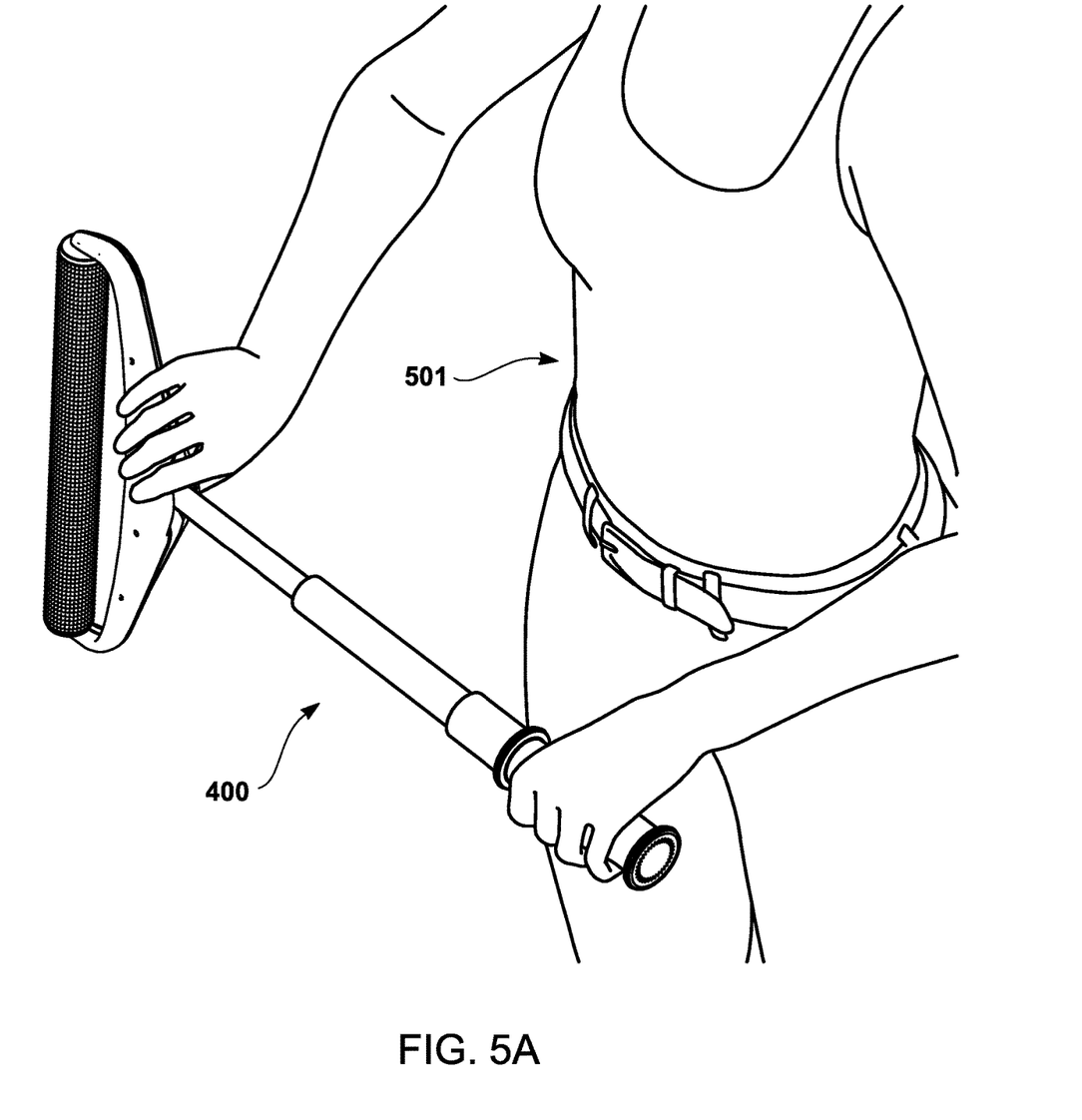
FIG. 5A illustrates the telescopic body-specific derma roller apparatus, without any actuators, being manually extended by a user.
Figure 5B:
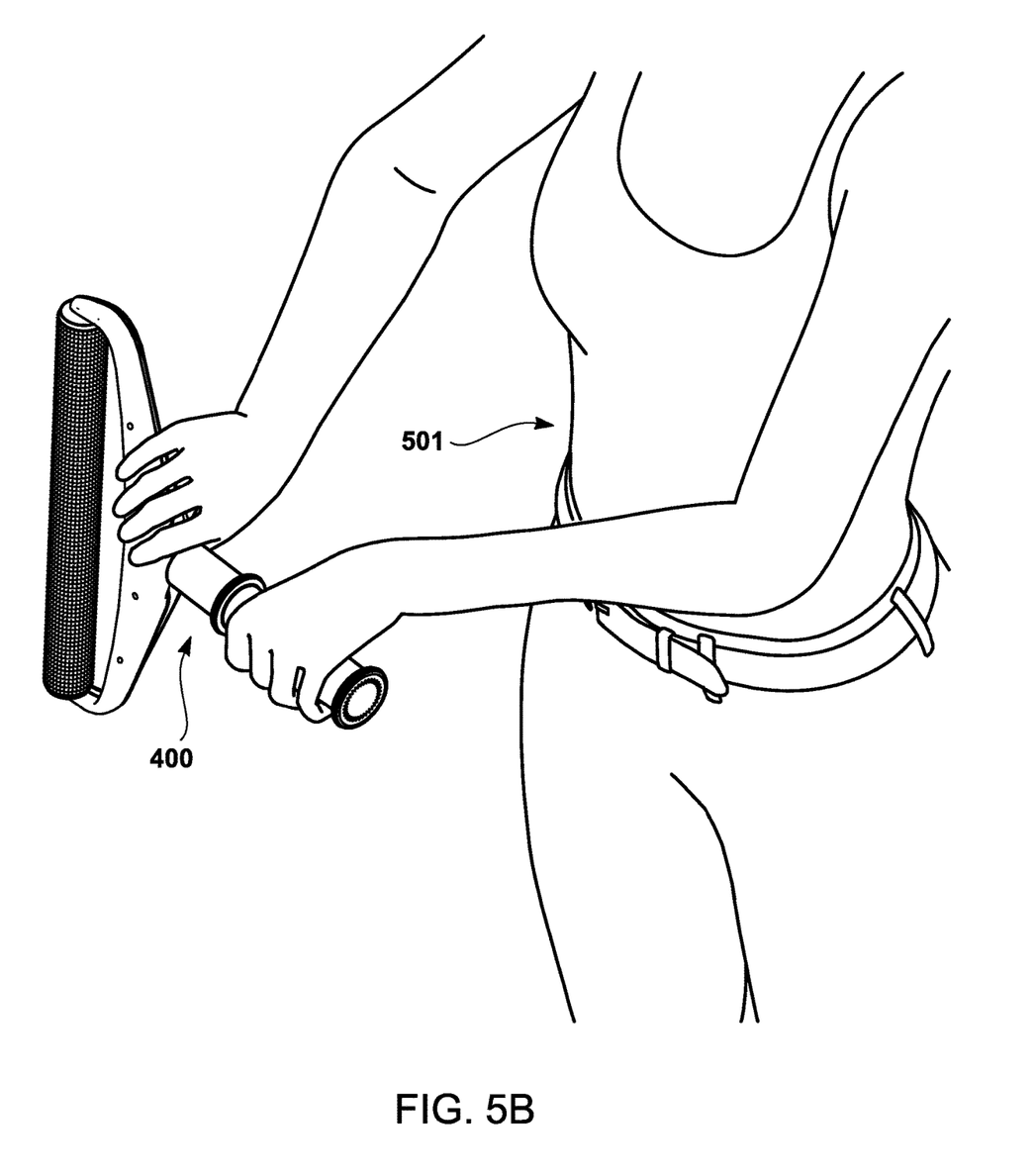
FIG. 5B illustrates the telescopic body-specific derma roller apparatus, without any actuators, being manually retracted by the user.

In yet another embodiment, the handle 104 may not have any buttons. In other words, the handle 104 may be manually extended and retracted without any activation. FIG. 5A illustrates the telescopic body-specific derma roller apparatus 400, without any actuators, being manually extended by a user 501. Additionally, FIG. 5B illustrates the telescopic body-specific derma roller apparatus 400, without any actuators, being manually retracted by the user 501.

Figure 6A:
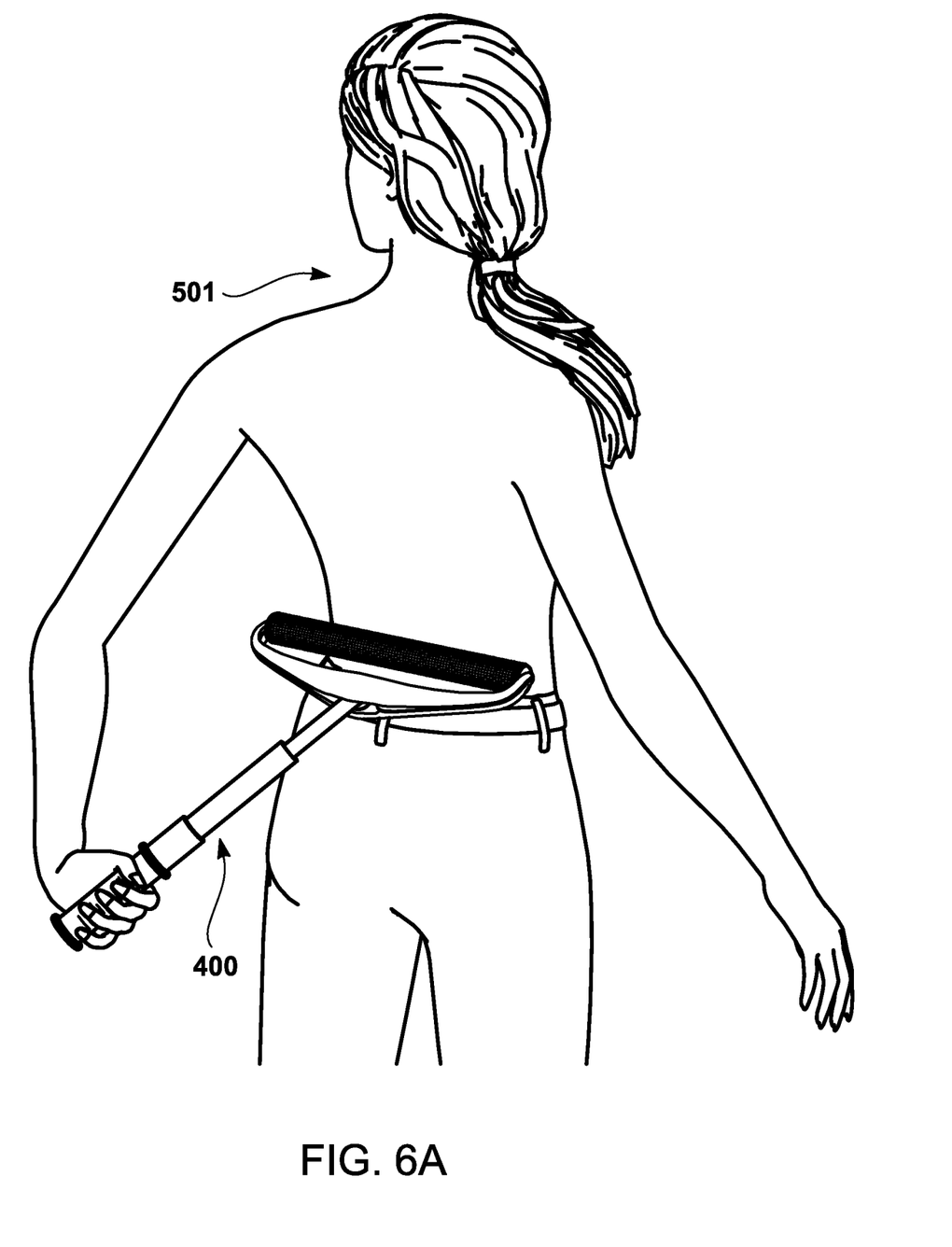
FIG. 6A illustrates the user derma rolling by moving the head in an upward motion starting from her lower back.
Figure 6B:
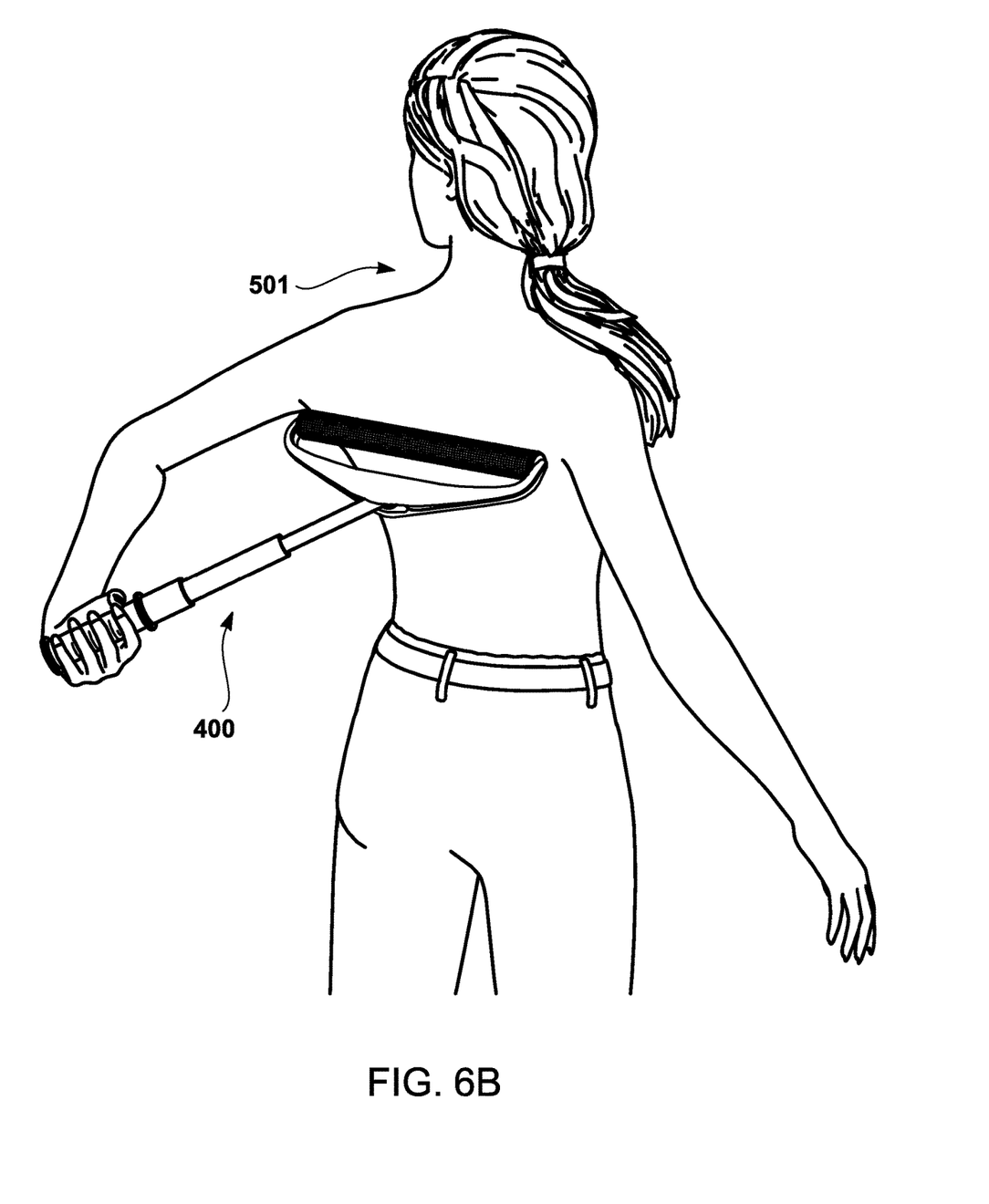
FIG. 6B illustrates the head having reached an endpoint of the linear path along the back of the user.

FIGS. 6A and 6B illustrates an example of the user 501 utilizing the telescopic body-specific derma roller apparatus 400 to perform body derma rolling on her lower back. (Alternatively, the body-specific derma roller apparatus 100, which may be non-telescopic, may be utilized instead.) For example, FIG. 6A illustrates the user 501 derma rolling by moving the head 101 in an upward motion starting from her lower back. The user 501 may change the angle of the head 101 via the swivel 103 to accommodate her particular manual dexterity; however, the motion of the head 101 remains substantially constant (e.g., within a deviation of less than thirty percent from the linear path). Accordingly, as illustrated in FIG. 6B, the head 101 has reached an endpoint of the linear path along the back of the user 501. The user 501 may have changed the angle of the handle 104, but the path of the head 101 remains substantially linear along the skin of the back of the user 501.

Figure 7:
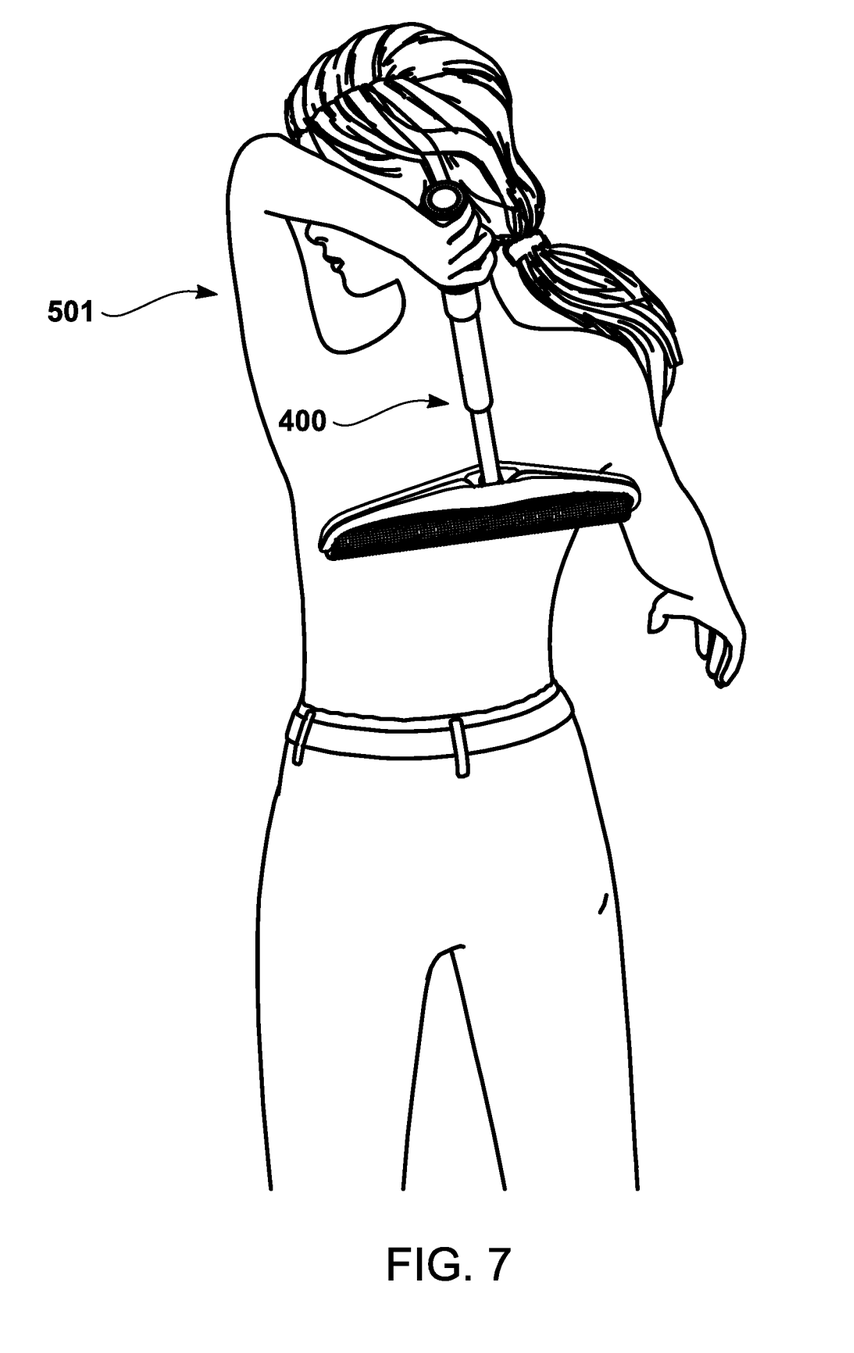
FIG. 7 illustrates the body-specific derma roller apparatus or the telescopic body-specific derma roller apparatus being utilized in the top portion of the back.
Figure 8:
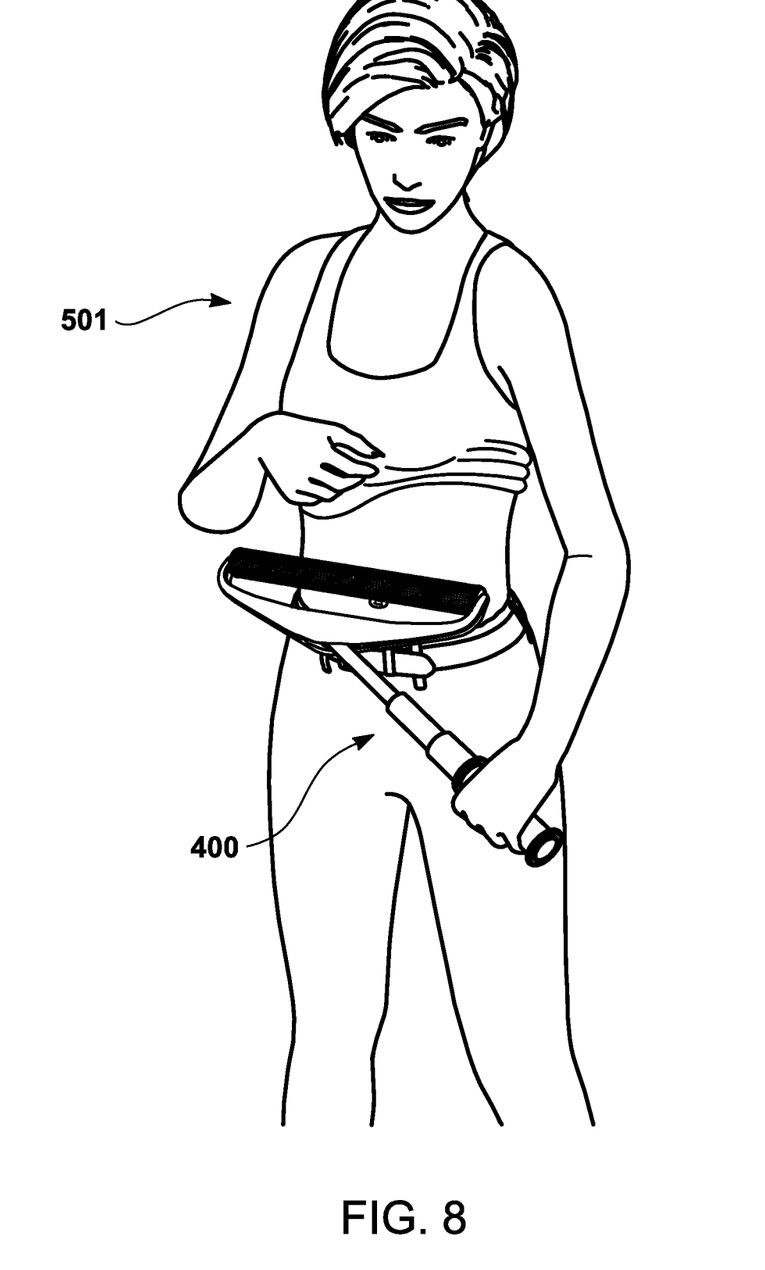
FIG. 8 illustrates the body-specific derma roller apparatus or the telescopic body-specific derma roller apparatus being utilized in an area that is visible to the user, such as the stomach.

The back is illustrated to depict how the user 501 is able, without seeing the head 101, to use the body-specific derma roller apparatus 100 or the telescopic body-specific derma roller apparatus 400 to perform a minimal number of derma rolling movements over a wide area of the skin by adjusting the angle of the handle 104. The body-specific derma roller apparatus 100 or the telescopic body-specific derma roller apparatus 400 also may be utilized in other areas, such as the top portion of the back, as illustrated in FIG. 7. As yet another example, the body-specific derma roller apparatus 100 or the telescopic body-specific derma roller apparatus 400 may be utilized in an area that is visible to the user 501, such as the stomach, as illustrated in FIG. 8. For example, the user 501 may utilize the body-specific derma roller apparatus 100 or the telescopic body-specific derma roller apparatus 400 to perform skincare rejuvenation in an area of the stomach having stretch marks.

The illustrated examples are provided only as examples. The body-specific derma roller apparatus 100 or the telescopic body-specific derma roller apparatus 400 may be utilized for derma rolling in a variety of other areas (e.g., arms, legs, buttocks, etc.).

Furthermore, the particular dimensions, shapes, contours, and other design features illustrated in the accompanying figures are provided only as examples—a variety of dimensions, shapes, contours, and other design features other than those illustrated may be utilized instead. Also, the fabrication of the body-specific derma roller apparatus 100 or the telescopic body-specific derma roller apparatus 400 may be from a variety of materials.

Additionally, the angulation of the swivel 103 with respect to the handle 104 is not limited to that as illustrated in FIGS. 3A and 3B. In other embodiments, the swivel 103 may be configured to allow the handle 104 to move with respect to an axis (e.g., pitch or roll) other than that which is perpendicular to the collinear plane 302 illustrated in FIGS. 3A and 3B.

It is understood that the apparatuses described herein may also be applied in other types of apparatuses. Those skilled in the art will appreciate that the various adaptations and modifications of the embodiments of the apparatuses described herein may be configured without departing from the scope and spirit of the present processes and systems. Therefore, it is to be understood that, within the scope of the appended claims, the present apparatuses may be practiced other than as specifically described herein.

I claim:

1. A derma roller apparatus comprising:
   a head comprising:
      a cylindrical member having a width in a range of four inches to twelve inches, and
      a plurality of needles situated around the cylindrical member, each of the plurality of needles having a length of at least five tenths millimeters;
   a swivel;

a connector that connects to a first endpoint of the head and a second endpoint of the head;

a handle operably attached to the connector via the swivel, the handle being configured to move along a yaw axis relative to the head via the swivel, the yaw axis being perpendicular to a collinear plane that is collinear with the head and the handle, the first endpoint and the second endpoint of the head being transverse to the collinear plane;

one or more stoppers that restrict movement of the handle within a predetermined angular range along the yaw axis; and a housing that encloses the swivel, the housing having a left wall and a right wall that are the one or more stoppers.

2. The derma roller apparatus of claim 1, wherein the housing is integrated within the connector.

3. The derma roller apparatus of claim 2, wherein the connector comprises a top portion and a bottom portion that are adhered to one another to encapsulate the swivel, the connector having a cavity through which the handle protrudes.

4. The derma roller apparatus of claim 3, wherein the swivel is configured to rotate only about the yaw axis without rotation about a pitch axis and a roll axis during movement of the derma roller apparatus along skin of a user.

5. The derma roller apparatus of claim 1, wherein the handle comprises a gripping portion.

6. The derma roller apparatus of claim 5, wherein the gripping portion has one or more finger grooves.

7. The derma roller apparatus of claim 5, wherein the gripping portion is fabricated with a ribbed texture.

8. The derma roller apparatus of claim 5, wherein the gripping portion has a guard and a pommel.

9. The derma roller apparatus of claim 1, wherein the handle is telescopic.

10. The derma roller apparatus of claim 9, further comprising a first actuator that activates extension of the handle and a second actuator that activates retraction of the handle.

11. The derma roller apparatus of claim 9, further comprising a single activator that activates both extension and retraction of the handle.

12. The derma roller apparatus of claim 1, wherein the handle comprises a handle stopper positioned along a surface of the handle, the handle stopper being configured to prevent slippage of a hand of a user during usage of the derma roller apparatus.

13. A derma roller apparatus comprising:

a head comprising:
  a cylindrical member having a width in a range of four inches to twelve inches, and
  a plurality of needles situated around the cylindrical member, each of the plurality of needles having a length of at least five tenths millimeters;

a swivel;

a connector that connects to a first endpoint of the head and a second endpoint of the head;

a telescopic handle operably attached to the connector via the swivel, the telescopic handle being configured to move along a yaw axis relative to the head via the swivel, the yaw axis being perpendicular to a collinear plane that is collinear with the head and the handle, the first endpoint and the second endpoint of the head being transverse to the collinear plane;

one or more stoppers that restrict movement of the handle within a predetermined angular range along the yaw axis; and a housing that encloses the swivel, the housing having a left wall and a right wall that are the one or more stoppers.

14. The derma roller apparatus of claim 13, wherein the housing is integrated within the connector.

15. The derma roller apparatus of claim 14, wherein the connector comprises a top portion and a bottom portion that are adhered to one another to encapsulate the swivel, the connector having a cavity through which the telescopic handle protrudes.

16. The derma roller apparatus of claim 15, wherein the swivel is configured to rotate only about the yaw axis without rotation about a pitch axis and a roll axis during movement of the derma roller apparatus along skin of a user.

17. The derma roller apparatus of claim 13, wherein the handle comprises a gripping portion.

\* \* \* \* \*